(12) United States Patent
Reeve et al.

(10) Patent No.: US 11,439,409 B2
(45) Date of Patent: Sep. 13, 2022

(54) CUTTING BLOCK

(71) Applicant: DEPUY IRELAND UNLIMITED COMPANY, Cork (IE)

(72) Inventors: Michael Reeve, North Yorkshire (GB); James Barnett, Leeds (GB)

(73) Assignee: DEPUY IRELAND UNLIMITED COMPANY, County Cork (IE)

(*) Notice: Subject to any disclaimer, the term of this patent is extended or adjusted under 35 U.S.C. 154(b) by 40 days.

(21) Appl. No.: 17/018,083

(22) Filed: Sep. 11, 2020

(65) Prior Publication Data

US 2021/0077122 A1  Mar. 18, 2021

(51) Int. Cl.
| | | |
|---|---|---|
| A61B 17/58 | (2006.01) | |
| A61B 17/60 | (2006.01) | |
| A61F 2/00 | (2006.01) | |
| A61B 17/15 | (2006.01) | |

(52) U.S. Cl.
CPC .......... *A61B 17/157* (2013.01); *A61B 17/151* (2013.01); *A61B 17/155* (2013.01)

(58) Field of Classification Search
CPC combination set(s) only.
See application file for complete search history.

(56) References Cited

U.S. PATENT DOCUMENTS

| | | |
|---|---|---|
| 3,727,928 A | 4/1973 | Benjamin |
| 4,710,075 A | 12/1987 | Davison |
| 4,952,213 A | 8/1990 | Bowman et al. |
| 5,100,409 A | 3/1992 | Coates et al. |
| 5,176,684 A | 1/1993 | Ferrante et al. |
| 5,356,414 A | 10/1994 | Cohen et al. |
| 5,415,662 A | 5/1995 | Ferrante et al. |
| 5,569,259 A | 10/1996 | Ferrante et al. |
| 5,571,194 A | 11/1996 | Gabriel |
| 5,601,563 A | 2/1997 | Burke et al. |
| 5,613,970 A | 3/1997 | Houston et al. |

(Continued)

FOREIGN PATENT DOCUMENTS

| | | |
|---|---|---|
| CH | 706593 A1 | 12/2013 |
| CN | 101742972 A | 6/2010 |

(Continued)

OTHER PUBLICATIONS

Zimmer NexGen LCCK, Surgical Technique for use with LCCK 4-in-1 Instrument, 2009, 52 pages.

(Continued)

*Primary Examiner* — Sameh R Boles (57) ABSTRACT

The invention relates to a cutting block for use in preparing a bone during orthopaedic surgery. The cutting block comprises a bone attachment face, and a front face opposing the bone attachment face. The cutting block further comprises at least a first group of bone pin holes, each hole being configured for removable receipt of a bone pin. The first group of pin holes includes at least two bone pin holes that extend between the bone attachment face and the front face. The at least two bone pin holes extend parallel to each other in an anterior-posterior direction. The at least two bone pin holes are offset from each other in at least one of a superior-inferior direction or a medial-lateral direction. The at least two bone pin holes are interconnected.

17 Claims, 5 Drawing Sheets

(56) References Cited

U.S. PATENT DOCUMENTS

| | | |
|---|---|---|
| 5,634,927 A | 6/1997 | Houston et al. |
| 5,681,316 A | 10/1997 | DeOrio et al. |
| 5,683,397 A | 11/1997 | Vendrely et al. |
| 5,702,460 A | 12/1997 | Carls et al. |
| 5,769,854 A | 6/1998 | Bastian et al. |
| 5,931,841 A | 8/1999 | Ralph |
| 5,976,147 A | 11/1999 | Lasalle et al. |
| 6,063,091 A | 5/2000 | Lombardo |
| 6,488,687 B1 | 12/2002 | Masini |
| 6,575,980 B1 | 6/2003 | Robie et al. |
| 6,945,145 B1 | 9/2005 | Kesinger et al. |
| 7,048,477 B2 | 5/2006 | Abrams |
| 7,497,874 B1 | 3/2009 | Metzger et al. |
| 7,547,327 B2 | 6/2009 | Collazo |
| 7,559,765 B2 | 7/2009 | Courvosier |
| 7,682,362 B2 | 3/2010 | Dees, Jr. |
| 7,744,600 B2 | 6/2010 | Rangaiah et al. |
| 7,963,968 B2 | 6/2011 | Dees, Jr. |
| 8,002,777 B2 | 8/2011 | Fox et al. |
| 8,038,681 B2 | 10/2011 | Koenemann |
| 8,187,280 B2 | 5/2012 | May et al. |
| 8,377,141 B2 | 2/2013 | McMinn |
| 8,425,524 B2 | 4/2013 | Aker et al. |
| 8,771,280 B2 | 7/2014 | Bailey et al. |
| 8,986,310 B2 | 3/2015 | Bailey et al. |
| 9,028,501 B2 | 5/2015 | Thomas et al. |
| 9,113,915 B2 | 8/2015 | Thomas et al. |
| 9,232,950 B2 | 1/2016 | Chaney |
| 9,282,981 B2 | 3/2016 | Chaney |
| 9,364,243 B2 | 6/2016 | Beedall |
| 9,579,113 B2 | 2/2017 | Thomas et al. |
| 9,636,122 B2 | 5/2017 | Chaney et al. |
| 9,962,173 B2 | 5/2018 | Thomas et al. |
| 10,098,646 B2 | 10/2018 | Ardito |
| 10,413,307 B2 | 9/2019 | Chaney |
| 10,470,898 B2 | 11/2019 | Hathaway et al. |
| 10,682,195 B2 | 6/2020 | Tredinnick |
| 2001/0001121 A1 | 5/2001 | Lombardo et al. |
| 2003/0114859 A1 | 6/2003 | Grusin et al. |
| 2004/0039450 A1 | 2/2004 | Griner et al. |
| 2004/0078043 A1 | 4/2004 | Masini |
| 2004/0087960 A1 | 5/2004 | Kinnett |
| 2004/0153087 A1 | 8/2004 | Sanford et al. |
| 2004/0225368 A1 | 11/2004 | Plumet et al. |
| 2005/0192588 A1 | 9/2005 | Garcia |
| 2006/0173463 A1 | 8/2006 | Dees |
| 2006/0195113 A1 | 8/2006 | Masini |
| 2006/0241634 A1 | 10/2006 | Tuttle et al. |
| 2007/0010890 A1 | 1/2007 | Collazo |
| 2007/0073305 A1 | 3/2007 | Lionberger et al. |
| 2007/0173850 A1 | 7/2007 | Rangaiah et al. |
| 2008/0091273 A1 | 4/2008 | Hazebrouck |
| 2008/0183177 A1 | 7/2008 | Fox et al. |
| 2008/0228189 A1 | 9/2008 | Fox et al. |
| 2008/0312659 A1 | 12/2008 | Metzger et al. |
| 2009/0088762 A1 | 4/2009 | Koenemann |
| 2009/0088763 A1 | 4/2009 | Aram et al. |
| 2009/0125114 A1 | 5/2009 | May et al. |
| 2009/0204115 A1 | 8/2009 | Dees, Jr. et al. |
| 2009/0222008 A1 | 9/2009 | Hogg et al. |
| 2010/0076441 A1 | 3/2010 | May et al. |
| 2010/0121334 A1 | 5/2010 | Couture et al. |
| 2010/0234850 A1 | 9/2010 | Dees, Jr. et al. |
| 2011/0093081 A1 | 4/2011 | Chana et al. |
| 2011/0218541 A1 | 9/2011 | Bailey et al. |
| 2011/0307067 A1 | 12/2011 | Dees |
| 2012/0310246 A1 | 12/2012 | Belcher et al. |
| 2012/0323334 A1 | 12/2012 | Jones et al. |
| 2013/0144293 A1* | 6/2013 | Wilkinson ......... A61B 17/1604 606/88 |
| 2013/0144296 A1 | 6/2013 | Yoko et al. |
| 2013/0165936 A1 | 6/2013 | Myers |
| 2013/0325014 A1 | 12/2013 | Sordelet et al. |
| 2013/0325016 A1 | 12/2013 | Sordelet et al. |
| 2013/0325018 A1 | 12/2013 | Thomas et al. |
| 2013/0325019 A1 | 12/2013 | Thomas et al. |
| 2013/0325021 A1 | 12/2013 | Sordelet et al. |
| 2013/0325136 A1 | 12/2013 | Thomas et al. |
| 2014/0276858 A1 | 9/2014 | Major et al. |
| 2016/0089161 A1 | 3/2016 | Ardito et al. |
| 2017/0333215 A1 | 11/2017 | Wolfson et al. |

FOREIGN PATENT DOCUMENTS

| | | |
|---|---|---|
| CN | 101849864 A | 10/2010 |
| CN | 101879099 A | 11/2010 |
| EP | 947169 A2 | 10/1999 |
| EP | 2145590 A1 | 1/2010 |
| EP | 2777550 A2 | 9/2014 |
| EP | 2777556 A2 | 9/2014 |
| FR | 2748389 A1 | 11/1997 |
| FR | 2752519 A1 | 2/1998 |
| FR | 2943528 A1 | 10/2010 |
| GB | 2323037 A | 9/1998 |
| JP | 11104155 A | 4/1999 |
| JP | 2009006066 A | 1/2009 |
| JP | 2010057527 A | 3/2010 |
| RU | 2168315 C2 | 6/2001 |
| RU | 2148960 C1 | 5/2020 |
| WO | 9625123 A2 | 8/1996 |
| WO | 9730661 A1 | 8/1997 |
| WO | 9852499 A1 | 11/1998 |
| WO | 0013597 | 3/2000 |
| WO | 2007041644 A1 | 4/2007 |
| WO | 2007114841 A1 | 10/2007 |
| WO | 2010019284 A1 | 2/2010 |
| WO | 2016126168 | 8/2016 |

OTHER PUBLICATIONS

DePuy Orthopaedics, Inc., Sigma Revision and M.B.T. Revision Tray, Surgical Technique, 2008, 82 pages.

Smith & Nephew, Legion, Revision Knee System, Surgical Technique, 2005, 40 pages.

Biomet, Vanguard SSK, Revision System, Surgical Technique, Feb. 2008, 64 pages.

GMK Revision, Surgical Technique, Ref. 99.27.12US rev. 1, 1999, 74 pages.

PFC Sigma RP-F, Specialist 2 Instruments, Surgical Technique, Performance in Flexion, 2007, 32 pages.

P.F.C. Sigma Rotating Platform Knee System with M.B.T Tray, Primary Procedure with a Curved or Posterior Stablised Implant, 2003, 43 pages.

LCS High Performance Instruments, Surgical Technique, 2008, 44 pages.

Sigma High Performance Instruments, Design Rationale, 2007, 12 pages.

Sigma High Performance Instruments, Classic Surgical Technique, 2010, 52 pages.

Attune Knee System Surgical Technique, 2013, 73 pages.

Redacted Memorandum with Appendix A, dated Jan. 26, 2010, outlining a surgical instrument evaluation that commenced in 2010, 37 pages.

"Reinstall Wave 1 Evaluation Surgical Technique," used during the surgical instrument evaluation that commenced in 2010, 36 pages.

Tray configuration cards showing the instruments used during the surgical instrument evaluation that commenced in 2010, 8 pages.

Declaration of Gary M. Lindsay dated Dec. 23, 2014, 5 pages.

International Search Report and Written Opinion, International Application No. PCT/US2017/033295, dated Dec. 18, 2017, 8 pages.

International Search Report issued in connection with International Application No. PCT/US2017/033307, dated Sep. 25, 2017, 13 pages.

International Search Report and Written Opinion, International Application No. PCT/US2017/033278, dated Nov. 21, 2017, 8 pages.

International Search Report, International Application No. PCT/US2017/033295, dated Sep. 4, 2017, 14 pages.

(56) References Cited

OTHER PUBLICATIONS

GB Search Report from corresponding GB Application No. GB1913436.0 dated Feb. 24, 2020, 1 page.
European Search Report, European Patent Application No. 20178555.7, dated Sep. 24, 2020, 8 pages.
Attune Revision Knee System Fixed Bearing Surgical Technique, DSUS/JRC/0217/2020 Rev. 2, 129094-191206 DSEM, (2019) 228 pgs.
Attune Knee System, Intuition Instruments Surgical Technique, DSUS/JRC/0316/1437 Rev. 6, DePuy Synthes (2017, 2018, 2019, 2020), 118 pages.
Attune Revision LPS Insert with S-ROM Noiles Rotating Hinge System and LPS System Surgical Technique, 103478192 Rev. 2, (2018), 92 pgs.

\* cited by examiner

CUTTING BLOCK

CROSS REFERENCE TO RELATED APPLICATION

This application claims priority to United Kingdom Application No. 1913436.0, filed Sep. 18, 2019, which is incorporated by reference in its entirety.

TECHNICAL FIELD

The present disclosure related generally to surgical instruments which are used to assist in the removal, repair or replacement of tissue, and particularly to cutting blocks for use in the resection of a bone.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis.

A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

From time-to-time, a revision knee surgery may need to be performed on a patient. In such a procedure, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

Figure 1:
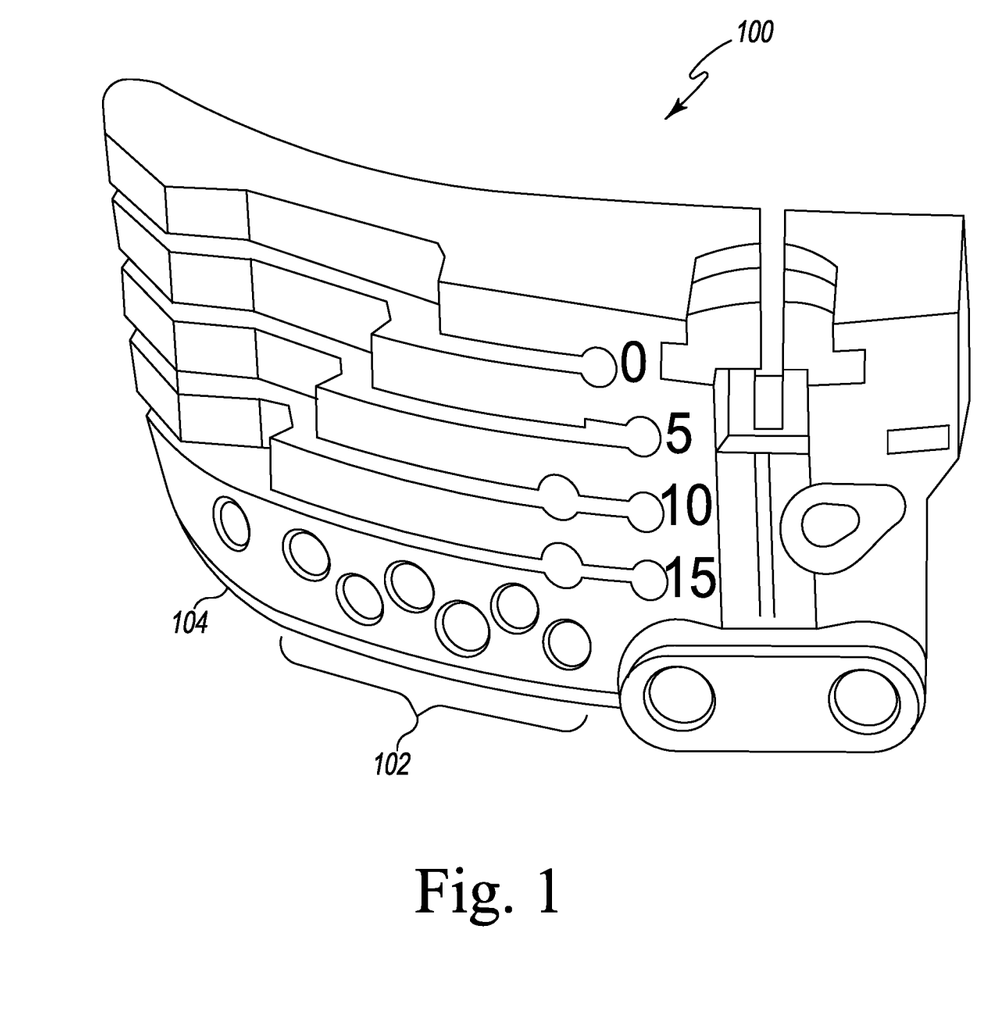
FIG. 1 is a photograph of a front view of a conventional tibial cutting block used in revision knee arthroplasty.

An example of a conventional cutting block used during revision surgery on a left tibia is shown in FIG. 1.

The tibial cutting block is often larger than those used during primary knee arthroplasty. This is so that the cutting block can accommodate the connection to an intramedullary surgical instrument, such as a reamer. Furthermore, the cutting block may include cutting slots for augments.

The revision tibial cutting block 100 shown in FIG. 1 includes an array of pin holes located near to the inferior face. The pin holes are provided in a linear array extending in a medial-lateral direction. In revision knee arthroplasty cases in which the patient's tibia is relatively small, the positioning of the bone pin array in this manner may make it impossible for the bone pins to be inserted into the proximal tibial metaphysis. As such, the tibial cutting block will not be securely mounted on the tibia. Any inadvertent movement of the cutting block during tibial resection may result in the tibia being resected at an unplanned tibial resection plane. An overly aggressive tibial cut might then require the surgeon to take remedial measures, such as the use of augments.

A need therefore exists for an improved tibial cutting block having an optimal placement of the pin hole array for secure mounting of the block onto the tibia, during revision knee arthroplasty, regardless of the size of the patient's bone.

SUMMARY

Aspects of the disclosure are set out in the accompanying independent and dependent claims. Combinations of features from the dependent claims may be combined with features of the independent claims as appropriate and not merely as explicitly set out in the claims.

Figure 2:
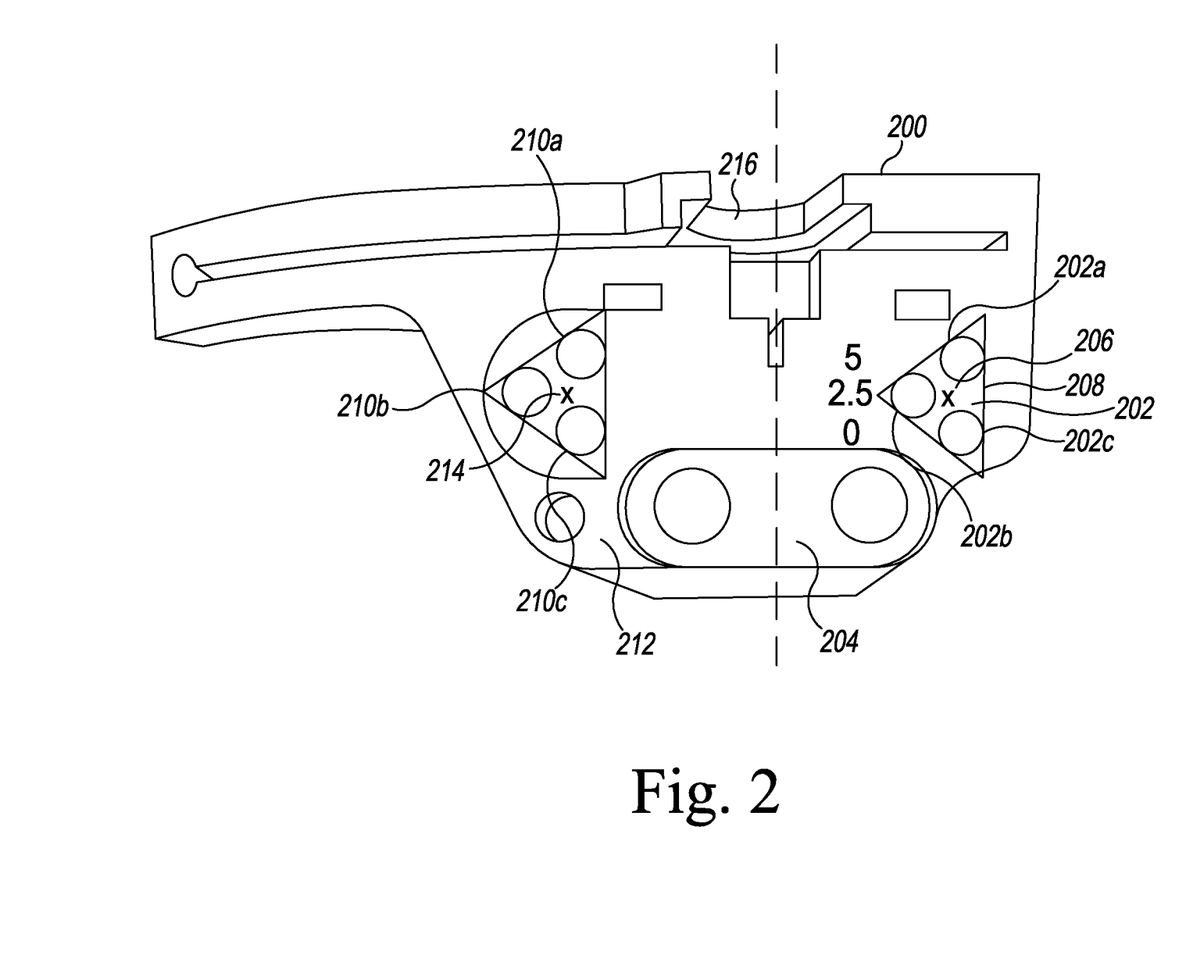
FIG. 2 is a photograph of a front view of a conventional tibial cutting block used in primary knee arthroplasty.

As shown in FIG. 2, conventional tibial cutting blocks used in primary knee arthroplasty typically include a bone pin hole array that has three holes arranged in an equilateral triangle format about a central point.

The bone pin holes in this exemplary tibial cutting block are labelled "0", "2.5" and "5". The centrepoint of each hole is vertically offset by about 2.5 mm. The block may be mounted on the tibia by inserting pins first through the holes marked "0". This technique will allow the block to be shifted inferiorly by 2.5 mm or 5 mm should additional resection be needed. In other constructions, the centrepoint of each hole is vertically offset such that the block may be shifted inferiorly by 2 mm or 4 mm should additional resection be needed. In some other constructions, the centrepoint of each hole is vertically offset such that the block to be shifted inferiorly by 1.5 mm or 3 mm should additional resection be needed.

Rather than simply replicating the bone pin hole array found in the primary tibial cutting blocks, in some constructions of a tibial cutting block according to the present invention, the most medially-placed hole of the tri-hole array is shifted laterally. Furthermore, the most medially-placed hole is interconnected with the other two bone pin holes. This arrangement is advantageous because it reduces the distance that the cutting block must be moved laterally when the block is shifted in the superior-inferior direction. As a result, this eliminates or minimises the extent that the lateral part of the cutting block impinges on the patella tendon during movement.

Advantageously, this design also reduces the overall width of the cutting block in the medial-lateral direction. Again, this eliminates or minimises the risk of impingement of the patella tendon, whilst also increasing the likelihood that the cutting block can be mounted on bone pins that have been securely inserted into the tibial metaphysis.

According to a first aspect, there is provided a cutting block for use in preparing a bone during orthopaedic surgery, the cutting block comprising:

a bone attachment face, and a front face opposing the bone attachment face, wherein the cutting block further comprises at least a first group of bone pin holes, each hole being configured for removable receipt of a bone pin, the first group of pin holes including at least two bone pin holes that extend between the bone attachment face and the front face, wherein the at least two bone pin holes extend parallel to each other in an anterior-posterior direction, wherein the at least two bone pin holes are offset from each other in at least one of a superior-inferior direction or a medial-lateral direction, and wherein the at least two bone pin holes are interconnected.

In some constructions of the cutting block, the at least two bone pin holes overlap. This overlap may be achieved by breaking through the walls to create a continuous, albeit offset hole.

In some further constructions, the cutting block includes a third pin hole which overlaps with the second pin hole. The third bone pin hole is located inferior of the second bone pin hole.

The third bone pin hole may also be offset from the second bone pin hole in a medial-lateral direction.

The third bone pin hole may also be aligned with the first pin hole in the medial-lateral direction.

Once the cutting block has been positioned on a bone, and an initial resection has be performed, the surgeon may decide that an additional resection is required. If this is the case, it may be considered desirable to maintain the orientation of the cutting block relative to the initial resection. This may be achieved by mounting the cutting block on at least two bone pins that are spaced apart and aligned in the medial-lateral direction. In order to do this, the cutting block may further comprise a second group of bone pin holes, which are spaced apart from the first group of bone pin holes.

Accordingly, the cutting block described herein may further comprise a second group of bone pin holes, wherein the second group of bone pin holes includes at least two bone pin holes extending between the bone attachment face and the front face, wherein the at least two bone pin holes extend parallel to each other in an anterior-posterior direction, wherein the at least two bone pin holes are offset from each other in at least one of a superior-inferior direction or a medial-lateral direction, and wherein the at least two bone pin holes are interconnected.

In terms of the geometry of the bone pin holes, each pin hole may be have a circular cross section when viewed from the anterior face of the cutting block. It is envisaged that the cutting block may be 3D printed, and accordingly to facilitate this method of manufacture each pin hole may have a polygonal cross section when viewed from the anterior face of the cutting block. For example, each bone pin hole may have a hexagonal or pentagonal cross section when viewed from the anterior face of the cutting block.

Advantageously, the geometry of each bone pin hole is selected such that at least three points of contact are maintained between the wall of the bone pin hole and the bone pin. This improves the stability of the connection, and hence the stability of the mounted cutting block.

The cutting block may be manufactured from a metal, for example stainless steel.

A surgeon may utilise one of the perimeter faces of the cutting block as a resection surface for guiding the resection of a bone to create a surgically-prepared surface. For example, the surgeon may utilise the superior face as a resection guide. However, it is also envisaged that in some constructions of the cutting block, a separate cutting guide slot, sized to receive a cutting tool, is provided within the cutting block.

The cutting block may be a tibial cutting block for use in either primary or revision knee arthroplasty. The cutting block may also be a femoral cutting block.

According to a second aspect, there is provided a surgical kit comprising a cutting block as herein described.

According to a third aspect, there is provided a method of surgically preparing a bone, the method comprising:
 inserting a bone pin into the bone,
 securing a cutting block to the bone, said cutting block comprising:
  a bone attachment face, and
  a front face opposing the bone attachment face,
 wherein the cutting block further comprises at least a first group of bone pin holes, the first group of pin holes including at least two bone pin holes that extend between the bone attachment face and the front face,
 wherein the at least two bone pin holes extend parallel to each other in an anterior-posterior direction,
 wherein the at least two bone pin holes are offset from each other in at least one of a superior-inferior direction or a medial-lateral direction, and
 wherein the at least two bone pin holes are interconnected,
 wherein the step of securing the cutting block to the bone includes:
  aligning at least one of the two bone pin holes with the bone pin, and
  sliding the cutting block in a posterior direction along the bone pin towards the bone.

According to a fourth aspect, there is provided a method of surgically preparing a proximal end of a tibia, the method comprising inserting a bone pin into the tibia,
 securing a tibial cutting block to the tibia, said cutting block comprising
  a bone attachment face, and
  a front face opposing the bone attachment face,
 wherein the cutting block further comprises at least a first group of bone pin holes, the first group of pin holes including at least two bone pin holes that extend between the bone attachment face and the front face,
 wherein the at least two bone pin holes extend parallel to each other in an anterior-posterior direction,
 wherein the at least two bone pin holes are offset from each other in at least one of a superior-inferior direction or a medial-lateral direction, and
 wherein the at least two bone pin holes are interconnected,
 wherein the step of securing the cutting block to the bone includes:
  aligning at least one of the two bone pin holes with the bone pin, and
  sliding the tibial cutting block in a posterior direction along the bone pin towards the tibia.

BRIEF DESCRIPTION OF THE DRAWINGS

Constructions of the cutting block will be described hereinafter, by way of example only, with reference to the accompanying drawings in which like reference signs relate to like elements and in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Constructions of the cutting block are described in the following with reference to the accompanying drawings.

A conventional tibial cutting block 100 used in revision knee arthroplasty is shown in FIG. 1. The block includes an array of bone pin holes 102 positioned near to the inferior face 104 of the cutting block. The array is arranged in the medial-lateral direction.

A conventional tibial cutting block 200 using in primary knee arthroplasty is shown in FIG. 2. The block includes a first group of bone pin holes 202 arranged on a lateral portion 204 of the block.

The first group of holes includes three bone pin holes, 202a, 202b, 202c arranged about a central point 206. The first bone pin hole 202a is the most superiorly located hole. The second bone pin hole 202b is placed inferior of the first bone pin hole 202a, and is also offset in the medial direction. The third bone pin hole 202c is placed inferior of the second bone pin hole 202b, and is offset in the lateral direction. When viewed from the front, also referred to as the anterior face of the cutting block, the first and third 202a, 202c bone pin holes are aligned in the medial-lateral direction.

The array of the first group of bone pins fits within a virtual equilateral triangle 208.

The bone pins holes 202a, 202b, and 202c extend parallel to each other in the anterior-posterior direction. The bone pins holes 202a, 202b, and 202c are not interconnected. Each hole is discrete, and there is "land" between each hole.

The cutting block also includes a second group of bone pin holes 210 arranged on a medial portion 212 of the block. The second group of holes includes three bone pin holes, 210a, 210b, 210c arranged about a central point 214.

The first bone pin hole 210a is the most superiorly located hole. The second hole 210b is placed inferior of the first bone pin hole 210a, and is also offset with respect to the first bone pin hole in the medial direction. The third bone pin hole 210c is placed inferior of the second bone pin hole 210b, and is offset with respect to second bone pin hole in the lateral direction. When viewed from the front, also referred to as the anterior face of the cutting block, the first and third 210a, 210c bone pin holes are aligned in the medial-lateral direction.

The bone pins holes 210a, 210b, and 210c extend parallel to each other in the anterior-posterior direction. The bone pins holes 210a, 210b, and 210c are not interconnected. Each hole is discrete, and there is "land" between each hole.

Each pin hole 210a, 210b and 201c has a center point, with a vertical spacing between center points of about 2.5 mm.

The cutting block includes a slot 216 which is configured for connection to a reamer placed within the intramedullary canal.

Figure 3:
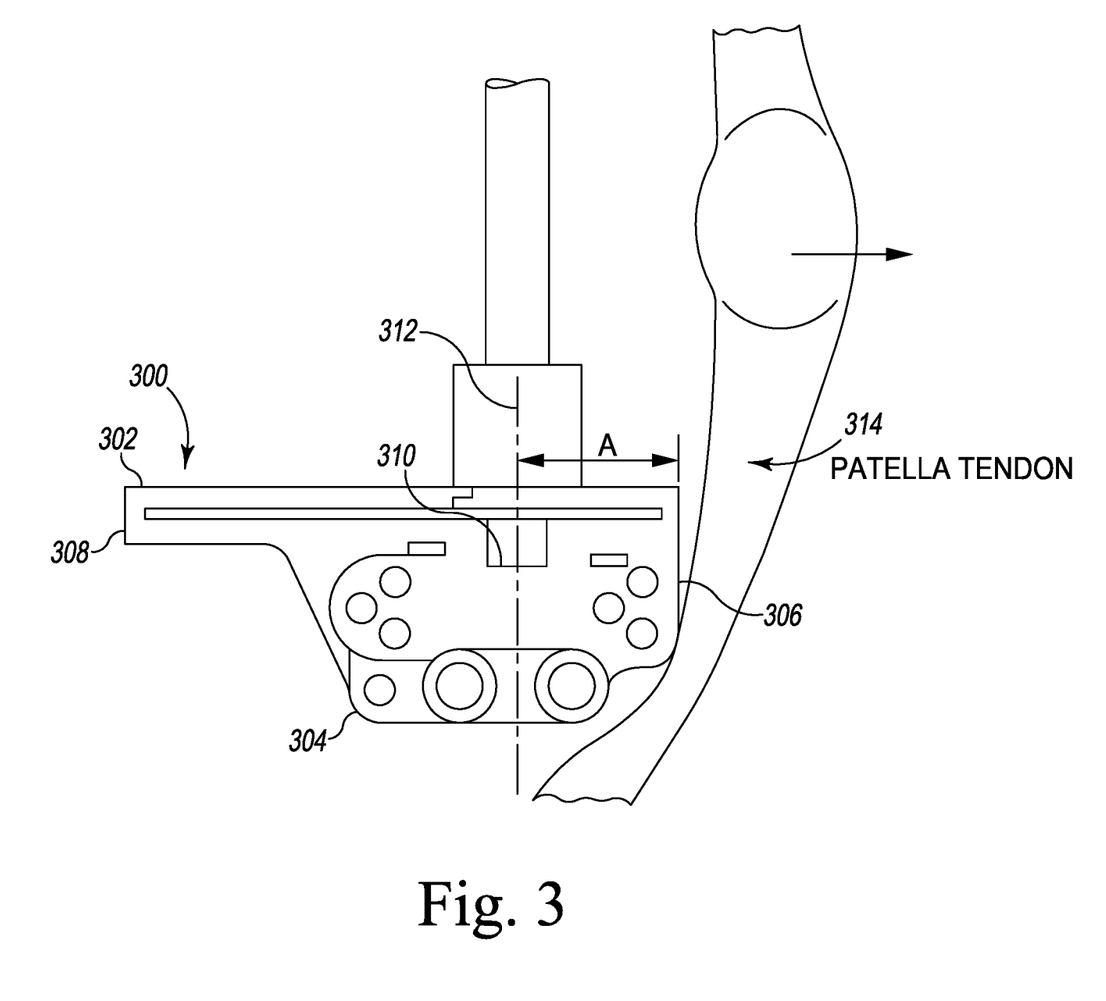
FIG. 3 is a schematic of a revision cutting block mounted on a tibia, the cutting block incorporates a similar bone pin hole array to that of the primary cutting block shown in FIG. 2.

FIG. 3 is a schematic of a hypothetical revision cutting block 300 mounted on a tibia. The cutting block incorporates a similar bone pin hole array to that provided on conventional primary cutting block, as shown in FIG. 2. The cutting block 300 has a superior face 302, an inferior face 304, a lateral face 306, and a medial face 308. The cutting block also includes a slot 310 for connection to a reamer inserted within the intramedullary canal. The slot has a central point 312. In order to be able to substitute the bone pin hole array provided on a conventional revision tibial cutting block (as shown in FIG. 1) with a bone pin hole array provided on a conventional primary tibial cutting block (as shown in FIG. 2), the cutting block requires a distance "A" between the central point 312 and the lateral face 306. The hypothetical block shown in FIG. 3 is wider than the conventional revision cutting blocks, and as can been seen this additional width causes the block to impinge on the patella tendon 314, and push it in a lateral direction. This can cause irritation to the patella tendon as the block moves laterally on the pin array during vertical translation of the block during surgery.

Figure 4:
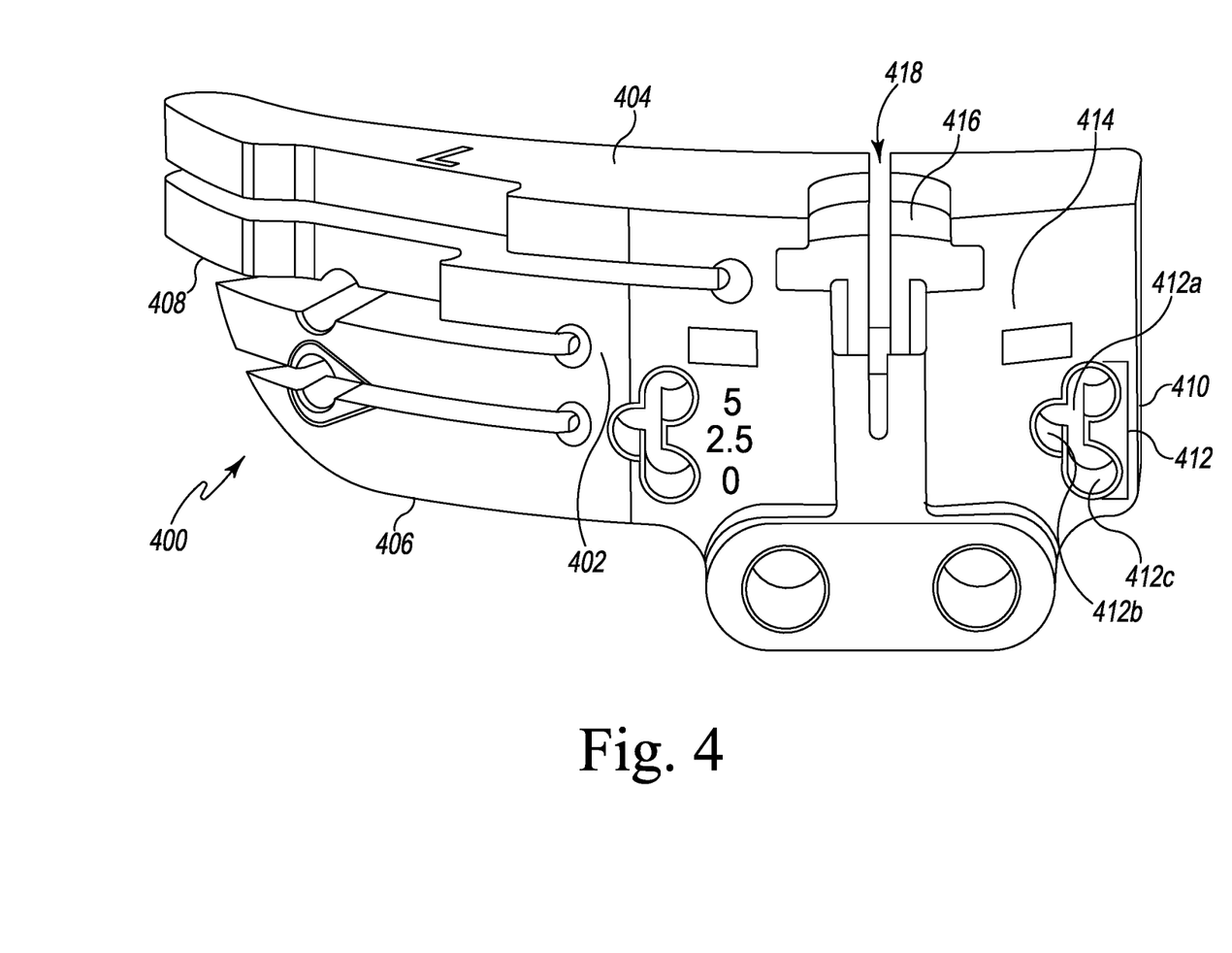
FIG. 4 is a schematic of a front view of a first construction of a revision tibial cutting block according to the invention.

Turning now to FIG. 4, there is shown a revision tibial cutting block 400 according to the first aspect of the invention. The cutting block has a bone attachment face (not shown), a front face 402 opposing the bone attachment face, a superior face 404, an inferior face 406, a medial face 408, and a lateral face 410.

The cutting block includes a first group of bone pin holes 412 arranged on a lateral portion 414 of the block.

The first group of holes includes three bone pin holes, 412a, 412b, 412c. The bone pin holes extend between the bone attachment face and the front face, and extend parallel to each other in an anterior-posterior direction.

The first bone pin hole 412a is the most superiorly located hole. The second bone pin hole 412b is placed inferior of the first bone pin hole 412a, and is also offset with respect to the first bone pin hole in the medial direction. The first and second bone pin holes 412a, 412b overlap with each other. The wall member of the first and second bone pin holes is omitted in the overlapping region. As a result, the two holes are interconnected in the overlapping region.

The third bone pin hole 412c is placed inferior of the second bone pin hole 412b, and is offset with respect to the second bone pin hole in the lateral direction.

The second and third bone pin holes 412b, 412c overlap with each other. The wall member of the second and third bone pin holes is omitted in the overlapping region. As a result, the two holes are interconnected in the overlapping region.

When viewed from the front face, also referred to as the anterior face of the cutting block, the first and third 412a, 412c bone pin holes are aligned in the medial-lateral direction.

Each pin hole 412a, 412b and 412c has a centre point, with a vertical spacing between centre points of about 2.5 mm. Hole 412c is labelled 0. Hole 412b is labelled 2.5. Hole 412a is labelled 5. The cutting block may be initially be mounted on the tibia by inserting a bone pin hole 412c. This technique will allow the block to be shifted by 2.5 mm or 5 mm should additional resection be needed. This is achieved by removing the cutting block, and remounting it onto the tibia with either bone pin hole 412b, or bone pin hole 412a receiving the bone pin.

The cutting block also includes a slot 416 for connection to a reamer inserted within the intramedullary canal. The slot has a central point 418.

Figure 5:
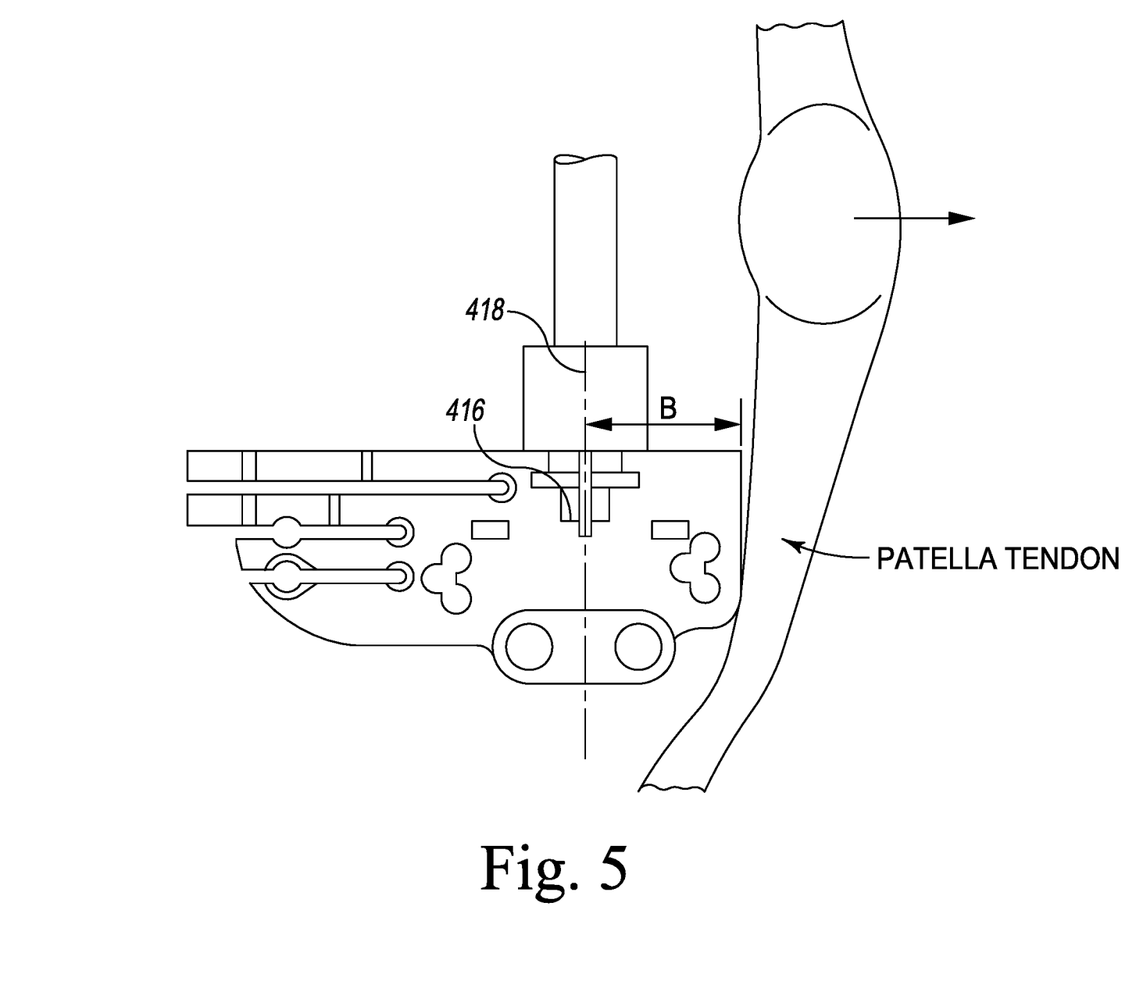
FIG. 5 is a schematic of a front view of the revision tibial cutting block of FIG. 4 mounted on a tibia.

The overlapping manner of the first, second and third bone pin holes 412a, 412b and 412c narrows the array of holes. As such, as shown in FIG. 5, the distance "B" between the central point 418 of the slot 416, and the lateral face 410 of the cutting block is reduced compared to the distance A (shown in FIG. 3). Hence, the lateral width of the cutting block is reduced, (minimising the risk of impingement of the patella), whilst maintaining the same functionality as the hypothetical cutting block shown in FIG. 3.

The invention claimed is:

1. A cutting block for use in preparing a bone during orthopaedic surgery, the cutting block comprising:
   a bone attachment face, and a front face opposing the bone attachment face, wherein the cutting block further comprises at least a first group of bone pin holes, each hole being configured for removable receipt of a bone pin, the first group of pin holes including at least two bone pin holes that extend between the bone attachment face and the front face, wherein the at least two bone pin holes extend parallel to each other in an anterior-posterior direction, wherein the at least two bone pin holes are offset from each other in at least one of a superior-inferior direction or a medial-lateral direction, and wherein the at least two bone pin holes are interconnected.

2. The cutting block of claim 1, wherein the at least two bone pin holes overlap.

3. The cutting block of claim 1, wherein the first group of bone pin holes further comprises at least a third bone pin hole, wherein the third bone pin hole is interconnected to the second bone pin hole.

4. The cutting block of claim 3, wherein the third bone pin hole overlaps with the second bone pin hole.

5. The cutting block of claim 3, wherein the third bone pin hole is located inferior of the second bone pin hole.

6. The cutting block of claim 5, wherein the third bone pin hole is offset from the second bone pin hole in a medial-lateral direction.

7. The cutting block of claim 6, wherein the first and third bone pin holes are aligned in the medial-lateral direction.

8. The cutting block of claim 1 wherein the cutting block further comprises a second group of bone pin holes, wherein the second group of bone pin holes includes at least two bone pin holes extending between the bone attachment face and the front face, wherein the at least two bone pin holes extend parallel to each other in an anterior-posterior direction, wherein the at least two bone pin holes are offset from each other in at least one of a superior-inferior direction or a medial-lateral direction, and wherein the at least two bone pin holes are interconnected.

9. The cutting block of claim 1, wherein the at least two bone pin holes have a circular cross section when viewed from the anterior face of the cutting block.

10. The cutting block of claim 1, wherein the at least two bone pin holes have a polygonal cross section when viewed from the anterior face of the cutting block.

11. The cutting block of claim 10, wherein the at least two bone pin holes have a pentagonal cross section when viewed from the anterior face of the cutting block.

12. The cutting block of claim 10, wherein the at least two bone pin holes have a hexagonal cross section when viewed from the anterior face of the cutting block.

13. The cutting block of claim 1, wherein the cutting block further includes a cutting guide slot sized to receive a cutting tool to resect bone to create a surgically-prepared surface.

14. The cutting block of claim 1, wherein the cutting block is a tibial cutting block.

15. The cutting block of claim 14, wherein the cutting block is a revision tibial cutting block.

16. The cutting block of claim 14, wherein the cutting block is a primary tibial cutting block.

17. The cutting block of any preceding claim 14, wherein the cutting block is a femoral cutting block.

* * * * *